United States Patent [19]

Gupta et al.

[11] Patent Number: 4,929,749

[45] Date of Patent: May 29, 1990

[54] PRODUCTION OF TEREPHTHALATE ESTERS BY DEGRADATIVE TRANSESTERIFICATION OF SCRAP OR VIRGIN TEREPHTHALATE POLYESTERS

[75] Inventors: Ved P. Gupta, LaSalle; Louis A. DuPont, Brossard, both of Canada

[73] Assignee: Synergistics Industries, Limited, Canada

[21] Appl. No.: 323,977

[22] Filed: Mar. 15, 1989

[51] Int. Cl.$^5$ .............................................. C07C 67/48
[52] U.S. Cl. .................................. 560/79; 528/308.1; 560/78; 560/92
[58] Field of Search .............................. 560/79, 78, 92

[56] References Cited

U.S. PATENT DOCUMENTS 3,037,048  5/1962  Lots et al. ............................ 560/79
4,578,502  3/1986  Cadmore .............................. 560/79

Primary Examiner—Werren B. Lone
Assistant Examiner—Vera C. Clarke
Attorney, Agent, or Firm—Larson and Taylor

[57] ABSTRACT

A process for the production of terephthalate esters having the following general formula (I).

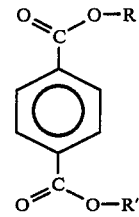

Substituents R and R' are the same or different and represent a straight chain or branched alkyl group having from 6 to 15 carbon atoms. The process comprises reacting a terephthalate polyester with a high molecular weight alcohol or mixture of high molecular weight alcohols in the presence of a catalyst and recovering the desired compound according to formula (I). This process is particularly useful for recycling scrap terephthalate polyesters such as polyethylene terephthalate and polybutylene terephthalate.

11 Claims, No Drawings

PRODUCTION OF TEREPHTHALATE ESTERS BY DEGRADATIVE TRANSESTERIFICATION OF SCRAP OR VIRGIN TEREPHTHALATE POLYESTERS

FIELD OF THE INVENTION

The present invention relates to a process for producing terephthalate esters through degradative transesterification of terephthalate polyesters. The reactants used for this process are terephthalate polyesters, preferably scrap terephthalate polyesters, thereby providing efficient means for recycling materials such as polyethylene terephthalate (PET) and polybutylene terephthalate (PBT). This process yields materials such as plasticizers that can be used in the preparation of products useful to the plastic industry.

BACKGROUND OF THE INVENTION

Terephthalate polyesters like polyethylene terephthalate (PET) and polybutylene terephthalate (PBT) are thermoplastic polymers that have been widely used in the plastic industry, especially for the preparation of films, fabrics, plastic containers of all kinds, textile materials and the like in the case of PET and for the preparation of auto body panels, fenders, relays, iron handles, lawn mower housings and the like in the case of PBT. However, with the growing use of terephthalate polyesters products also came the waste disposal problems and expenses encountered by both the manufacturers and the users.

There is at present a certain number of avenues available to recycle or degrade terephthalate polyesters. For example, high molecular weight polymer PET has been recycled by either grinding solid scrap PET and using the ground material as a filler or by partially depolymerizing the high molecular weight polymer in the presence of a monomer to produce a low molecular weight polymer. These types of processes are disclosed in U.S. Pat. No. 3,037,048.

In U.S. Pat. No. 3,037,048, Lotz discloses a process through which scrap PET products such as filaments, films, fabrics and others are recycled to regenerate the compound dimethyl terephthalate (DMT). This process involves the depolymerization of PET and transesterification in the presence of methanol to yield DMT.

Furthermore, U.S. Pat. No. 4,578,502 issued to Cudmore discloses the use of PET scrap for recovering ethylene glycol and either terephtalic acid or dimethylterephthalate. The process includes depolymerization of a slurry of scrap PET by hydrolysis or methanolysis, and subsequently crystallization of the desired product. The disclosure of U.S. Pat. No. 4,578,502 is limited to the production of dimethyl terephthalate. In fact, at column 3, lines 22–28 of this document, it is stated that it is preferable not to use alcohols of a higher molecular weight than methanol.

Thus, most of the PET recycling processes using transesterification presently known in the art are mainly aimed at producing starting materials that could be used for the synthesis of new PET products. Therefore, it would be interesting to provide a one step process for the recycling of PET that would yield a product that could be readily used either in the plastics industry or otherwise. Plasticizers are a good example of useful and readily usable products for the plastics industry.

Plasticizers are crucial constituents in the preparation of some plastic products. For example, di octyl terephthalate (DOTP) is particularly useful to the PVC industry. Esters of this type can be synthesized mainly by reacting terephthalic acid with a suitable alcohol. Unfortunately, in this case, the esterification reaction is very slow, thereby making the process economically undesirable. Alternatively, the transesterification of di methyl terephthalate to DOTP through its reaction with 2-ethyl hexanol is an interesting reaction that yields DOTP rather quickly.

Terephthalate polyesters are polymers that are widely used in the plastics industry despite the serious disposal and recycling problems encountered by their users. Therefore, suitable recycling alternatives that would yield a product of good commercial value would be highly desirable.

SUMMARY OF THE INVENTION

In accordance with the present invention, there is provided a process for producing a compound having the following general formula (I):

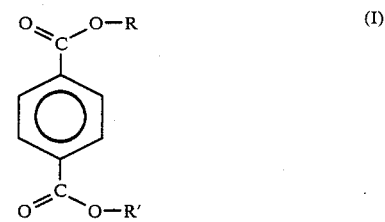

In formula (I), substituents R and R' are the same or different and represent a straight chain or branched alkyl group having from 6 to 15 carbon atoms. The process comprises reacting a terephthalate polyester with a high molecular weight alcohol or mixture of high molecular weight alcohols in the presence of a catalyst and recovering the compound according to formula (I). Preferably, the terephthalate ester source will come from scrap terephthalate polyesters although any suitable terephthalate ester source could be used in the context of the present invention. The carbon atom content of the alcohol to be used in the process of the present invention will correspond to the desired carbon atom content of substituents R and R'.

Hence, it has been discovered that scrap terephthalate polyesters can be successfully recycled through transesterification with higher alcohols to yield valuable compounds. Preferably, terephthalate polyesters such as scrap PET or PBT can be recycled to desirable products useful to the plastic industry. It is to be noted, that in the context of the present invention, the term "recycle" when used herein is intended to define a process through which scrap material such as PET or PBT is used as a starting material for producing terephthalate esters such as plasticizers. For example, plasticizers such as di octyl terephthalate (DOTP) can be prepared using the process of the present invention at a cost that is comparable to the cost of the currently available processes.

The process of the present invention constitutes a clearly unexpected advance in PET recycling for example, considering the fact that the teachings of pertinent literature on PET recycling such as U.S. Pat. No. 4,578,502 clearly leads away from the use of higher alcohols in reactions involving PET scrap.

The advantages of the process of the present invention would be more readily illustrated by referring to the following description.

DETAILED DESCRIPTION OF THE INVENTION

The present invention relates to a process for producing terephthalate polyesters. The process is useful for recycling solid scrap terephthalate polyester resins such as the PET resin that can be found in plastic bottles, films and the like as well as PBT resin that can be found in body panels, fenders and the like.

Generally speaking, the process of the present invention involves the transesterification of a terephthalate polyester at temperatures that can vary between 160° and 260° C. preferably between 185° to 260° C. using a straight or branched alcohol having a carbon atom content ranging from 6 to 15 inclusively. It is to be mentioned that since transesterification reactions are performed with catalysts, the use of any suitable esterification or catalyst may be contemplated. Catalysts such as p-toluenesulfonic acid or stannous oxalate are preferred in the context of the present invention.

The temperature at which transesterification of most terephthalate polyesters occurs is relatively high. It will usually range between 160° and 260° C. Hence, a number of suitable alcohols that could be used in the process of the present invention have boiling points that are lower than the desirable transesterification temperature. This minor difficulty may be overcome by pressurizing the reaction vessel or by adding suitable amounts of the final product to the initial reaction mixture in order to raise its overall boiling point.

It is to be noted that in certain instances it may be desirable to use a mixture of alcohols for performing the process of the present invention. In the case of an alcohol mixture containing two alcohols, three different compounds would be obtained, one where both substituants R and R' would bear the alkyl portion of the first alcohol, one where both substituants R and R' would bear the alkyl portion of the second alcohol and one where substituants R and R' would bear different alkyl groups. The proportions of the alcohols forming the desired alcohol mixture will vary depending on the targetted composition of the final product.

Typically, 500 grams of polyethylene terephthalate scrap are mixed with between 800 and 1500 g of a given alcohol along with small amounts of a catalyst such as stannous oxalate. The resulting solution is heated to a temperature ranging between 185° and 235° C. Once the optimal temperature has been reached, it should be maintained for a period ranging from 3 to 6 hours depending on the type of alcohol used. In instances where the boiling point of the alcohol or mixture of alcohols is lower than the optimal reaction temperature, it is necessary to pressurize the reaction vessel or add suitable amounts of the final product. Undesirable reaction by-products such as ethylene glycol may distill off during the reaction process. It is to be noted that the removal of glycol and/or the addition of an excess of alcohol may accelerate the transesterification reaction.

In most cases, between 700 and 1400 grams of the desired final product will be obtained for each 500 grams of PET reacted with the suitable alcohol or alcohol mixture.

Typical examples of the products that can be obtained using the process of the present invention include di octyl isodecyl terephthalate, di isodecyl terephthalate, di octyl terephthalate, di normal octyl decyl terephthalate, di normal octyl isodecyl terephthalate and di isononyl terephthalate.

The following examples are included in order to further illustrate rather than limit the scope of the present invention.

EXAMPLE 1

Preparation of di isodecyl terephthalate (DIDTP)

To 1 liter of isodecanol was added 64 grams of solid polyethylene terephthalate and 0.45 g of tin catalyst such as stannous oxalate. The mixture was then heated from room temperature to 220° C. over a period of two hours and maintained at 220° C. for an additional period of two hours.

The temperature was then decreased from 220° C. to 196° C. over a further period of two hours after which gas chromatography analysis of the final product revealed the presence of DIDTP. Removal of residual isodecanol and ethylene glycol was achieved by steam distillation of DIDTP under vacuum. The distillation vessel was heated from room temperature to 164° C. over a period of two and a half hours after which the desired product was recovered.

EXAMPLE 2

Preparation of di octyl terephthalate (DOTP)

230 ml of 2-ethyl hexanol were added to 200 ml of DOTP, 0.45 g of tin catalyst such as stannous oxalate and 100 grams of solid scrap PET. The temperature was raised from room temperature to 236° C. over a period of time of approximately three hours at which point 60 ml of 2-ethyl hexanol was added to the mixture. The mixture was then further heated for two and a half hours after which 20 ml of 2-ethylhexanol was added. The temperature was then maintained at 230° C. for an additional five hours. The removal of residual 2-ethyl hexanol and ethylene glycol was achieved by steam distillation of DOTP under vacuum. The distillation vessel was heated from room temperature to 161° C. over a period of two hours after which the final product, approximately 150 ml of additional DOTP was recovered.

EXAMPLE 3

Preparation of di normal octyl decyl terephthalate (DNODTP)

To 500 ml of an alcohol mixture containing normal octanol and normal decanol and sold under the tradename ALFOL 810 was added 172 grams of solid PET scrap as well as 0.3 g of tin catalyst. The mixture was heated from room temperature to 217° C. over a period of approximately three and a half hours and then maintained at that temperature for an additional three hours. Gas chromatography analysis revealed the presence of the desired product. The removal of residual alcohol and glycol was achieved by steam distillation of DNODTP under vacuum. The distillation vessel was heated from room temperature to 136° C. over a period of four hours after which the desired product was recovered.

EXAMPLE 4

Preparation of di normal octyl isodecyl terephthalate (DNOIDTP)

To an alcohol mixture containing 250 ml of n-octanol and 250 ml of isodecanol were added 192 grams of solid scrap PET as well as 0.3 grams of tin catalyst. The solution was then heated up from room temperature to 216° C. over a period of approximately two hours after which it was further heated up to 232° C. for an additional period of four hours. Gas chromatography revealed the presence of the desired product. The removal of residual alcohol and glycol was achieved by the steam distillation of DNOIDTP under vacuum. The distillation vessel was heated from room temperature to 177° C. over a period of six hours after which the desired product was recovered.

EXAMPLE 5

Preparation of di isodecyl terephthalate (DIDTP)

To 475 grams of isodecanol was added 192 grams of solid scrap PET as well as 0.3 gram of tin catalyst such as stannous oxalate. The solution was then rapidly heated up from room temperature to 216° C. after which the temperature was slowly raised to 242° C. over a total period of approximately six hours. Gas chromatography of the final solution demonstrated the presence of DIDTP. The removal of residual isodecanol and ethylene glycol was achieved by steam distillation of DIDTP under vacuum. The distillation vessel was heated from room temperature to 164° C. over a period of approximately four hours after which approximately 425 g of the desired product was recovered. This indicated an approximate yield of 95 percent.

EXAMPLE 6

Preparation of di isononyl terephthalate (DINTP)

To 615 ml of isononanol were added 230 grams of solid scrap PET and 0.3 g of tin catalyst such as stannous oxalate. The solution was then slowly heated up from room temperature to 215° C. over a period of approximately 4½ hours after which gas chromatography clearly demonstrated the presence of the desired product. The removal of residual isononanol and ethylene glycol was achieved by steam distillation of DINTP under vacuum. The distillation vessel was heated from room temperature to 150° C. over a period of three and a half hours after which the desired product was recovered.

EXAMPLE 7

Preparation of di octyl isodecyl terephthalate (DOIDTP)

To 1 L of 2-ethyl hexanol were added 110 grams of solid scrap polyethylene terephthalate as well as 0.3 grams of a toluenesulfonic acid catalyst. The solution was then heated from room temperature to 187° C. over a period of approximately two hours. After heating at 187° C. for approximately one hour, 500 ml of isodecanol was slowly added to the solution over a period of two and a half hours after which the temperature reached 200° C. Gas chromatography analysis confirms the presence of the desired product. The removal of residual alcohol and glycol was achieved by steam distillation of DOIDTP under vacuum. The distillation vessel was heated from room temperature to 176° C. over a period of three and a half hours after which the desired product is recovered.

Various changes may be made to the embodiments described herein without departing from the scope of the present invention which is limited only by the following claims.

The embodiments of the invention in which an exclusive property or privilege is claimed are defined as follows:

1. A process for producing a compound having the following formula (I):

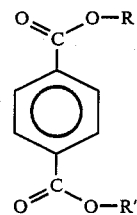

wherein R and R' are the same or different and represent a straight chain or branched alkyl group having from 6 to 15 carbon atoms, said process comprising, reacting a terephthalate polyester with an alcohol or mixture of alcohols having from six to 15 carbon atoms in the presence of a catalyst and recovering the compound according to formula (I).

2. The process of claim 1 wherein the reaction is carried out at a temperature ranging between 160° and 260° C.

3. The process of claim 1 wherein the terephthalate polyester is polyethylene terephthalate.

4. The process of claim 1 wherein the terephthalate polyester is polybutylene terephthalate.

5. The process of claim 3 wherein the alcohol is a mixture of 2-ethyl hexanol and isodecanol and the compound according to formula (I) is di octyl isodecyl terephthalate.

6. The process of claim 3 wherein the alcohol is isodecanol and the compound according to formula (I) is di isodecyl terephthalate.

7. The process of claim 3 wherein the alcohol is 2-ethyl hexanol and the compound according to formula (I) is di octyl terephthalate.

8. The process of claim 3 wherein the alcohol is a mixture of normal octanol and decanol and wherein the compound according to formula (I) is di normal octyl decyl terephthalate.

9. The process of claim 3 wherein the alcohol is a mixture of normal octanol and isodecanol and the compound according to formula (I) is di normal octyl isodecyl terephthalate.

10. The process of claim 3 wherein the alcohol is isononanol and the compound according to formula (I) is di isononanol terephthalate.

11. A process for recycling scrap polyethylene terephthalate, said process comprising reacting scrap polyethylene terephthalate with a high molecular weight alcohol having from 6 to 15 carbon atoms or a mixture of high molecular weight alcohols having from 6 to 15 carbon atoms in the presence of a catalyst at a temperature ranging from 185° to 235° C. and recovering the desired terephthalate ester.

* * * * *

REEXAMINATION CERTIFICATE (1725th)

United States Patent [19]
Gupta et al.

[11] B1 4,929,749
[45] Certificate Issued   Jun. 23, 1992

[54] PRODUCTION OF TEREPHTHALATE ESTERS BY DEGRADATIVE TRANSESTERIFICATION OF SCRAP OR VIRGIN TEREPHTHALATE POLYESTERS

[75] Inventors: Ved P. Gupta, LaSalle; Louis A. DuPont, Brossard, both of Canada

[73] Assignee: Synergistics Industries Limited

Reexamination Request:
No. 90/002,134, Sep. 12, 1990

Reexamination Certificate for:
Patent No.: 4,929,749
Issued: May 29, 1990
Appl. No.: 323,977
Filed: Mar. 15, 1989

[51] Int. Cl.⁵ .............................................. C07C 67/48
[52] U.S. Cl. .................................. 560/79; 528/308.1; 560/78; 560/92
[58] Field of Search ........................... 560/78, 79, 92

[56] References Cited

U.S. PATENT DOCUMENTS

| | | | |
|---|---|---|---|
| 3,037,048 | 5/1962 | Lots et al. | 560/79 |
| 4,002,667 | 1/1977 | Thompson | 560/92 |
| 4,578,502 | 3/1986 | Cadmore | 560/79 |

FOREIGN PATENT DOCUMENTS

48-097831A 12/1973 Japan.

*Primary Examiner*—Jose G. Dees

[57] ABSTRACT

A process for the production of terephthalate esters having the following general formula (I).

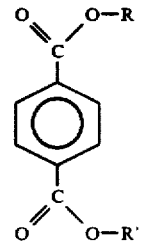

Substituents R and R' are the same or different and represent a straight chain or branched alkyl group having from 6 to 15 carbon atoms. The process comprises reacting a terephthalate polyester with a high molecular weight alcohol or mixture of high molecular weight alcohols in the presence of a catalyst and recovering the desired compound according to formula (I). This process is particularly useful for recycling scrap terephthalate polyesters such as polyethylene terephthalate and polybutylene terephthalate.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-11 are cancelled.

* * * * *